(12) United States Patent
Rezai et al.

(10) Patent No.: US 8,112,154 B2
(45) Date of Patent: Feb. 7, 2012

(54) SYSTEMS AND METHODS FOR NEUROMODULATION USING PRE-RECORDED WAVEFORMS

(75) Inventors: Ali Rezai, Shaker Heights, OH (US); Andre Machado, Beachwood, OH (US); Keith Carlton, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 670 days.

(21) Appl. No.: 11/943,344

(22) Filed: Nov. 20, 2007

(65) Prior Publication Data
US 2008/0208284 A1 Aug. 28, 2008

Related U.S. Application Data

(63) Continuation-in-part of application No. 11/522,029, filed on Sep. 15, 2006, now Pat. No. 7,715,912, which is a continuation-in-part of application No. 11/404,006, filed on Apr. 13, 2006.

(60) Provisional application No. 60/671,011, filed on Apr. 13, 2005.

(51) Int. Cl.
*A61N 1/05* (2006.01)
(52) U.S. Cl. .............. 607/45; 607/46; 607/48; 607/58
(58) Field of Classification Search .......... 607/5, 30, 607/45, 46, 57, 59, 48, 68
See application file for complete search history.

(56) References Cited

U.S. PATENT DOCUMENTS

| | | | |
|---|---|---|---|
| 4,841,973 | A | 6/1989 | Stecker |
| 5,222,494 | A | 6/1993 | Baker, Jr. |
| 5,304,206 | A | 4/1994 | Baker, Jr. et al. |
| 5,593,427 | A | 1/1997 | Gliner et al. |
| 5,601,612 | A | 2/1997 | Gliner et al. |
| 5,607,454 | A | 3/1997 | Cameron et al. |
| 5,620,470 | A | 4/1997 | Gliner et al. |
| 5,749,904 | A | 5/1998 | Gliner et al. |
| 5,749,905 | A | 5/1998 | Gliner et al. |
| 5,978,713 | A | 11/1999 | Prutchi et al. |

(Continued)

FOREIGN PATENT DOCUMENTS
EP 1559369 8/2005
(Continued)

OTHER PUBLICATIONS

PCT International Search Report and the Written Opinion of the International Searching Authority of the ISA dated Feb. 19, 2009.

*Primary Examiner* — Niketa Patel
*Assistant Examiner* — Joseph Stoklosa
(74) *Attorney, Agent, or Firm* — Kenyon & Kenyon LLP

(57) ABSTRACT

Methods for neuromodulation using waveform signals. In certain embodiments, an input waveform is obtained from a signal source site in a source subject and an output waveform is applied to a target site in a target subject. The source subject is a human or animal and the signal source site is in the nervous system, including the brain. The source subject and target subject are the same subjects or different subjects. The output waveform is identical to the input waveform or derived from the input waveform. In some embodiments, the output waveform is modified in response to physiologic feedback. Also provided are systems for neuromodulation using waveform signals.

16 Claims, 5 Drawing Sheets

U.S. PATENT DOCUMENTS

| | | | |
|---|---|---|---|
| 6,016,449 A | 1/2000 | Fischell et al. | |
| 6,029,090 A | 2/2000 | Herbst | |
| 6,128,538 A | 10/2000 | Fischell et al. | |
| 6,253,109 B1 * | 6/2001 | Gielen | 607/45 |
| 6,393,325 B1 | 5/2002 | Mann et al. | |
| 6,442,432 B2 | 8/2002 | Lee | |
| 6,507,759 B1 | 1/2003 | Prutchi et al. | |
| 6,560,490 B2 | 5/2003 | Grill et al. | |
| 6,579,280 B1 | 6/2003 | Kovach et al. | |
| 6,609,031 B1 | 8/2003 | Law et al. | |
| 6,631,297 B1 | 10/2003 | Mo | |
| 6,654,642 B2 | 11/2003 | North et al. | |
| 6,662,053 B2 | 12/2003 | Borkan | |
| 6,684,106 B2 | 1/2004 | Herbst | |
| 6,690,974 B2 | 2/2004 | Archer et al. | |
| 6,692,315 B1 | 2/2004 | Soumillion et al. | |
| 6,748,276 B1 | 6/2004 | Daignault, Jr. et al. | |
| 6,850,802 B2 | 2/2005 | Holsheimer | |
| 6,937,891 B2 | 8/2005 | Leinders et al. | |
| 6,944,501 B1 | 9/2005 | Pless | |
| 7,008,413 B2 | 3/2006 | Kovach et al. | |
| 7,058,446 B2 | 6/2006 | Schuler et al. | |
| 7,082,333 B1 | 7/2006 | Bauhahn et al. | |
| 7,127,297 B2 | 10/2006 | Law et al. | |
| 7,142,923 B2 | 11/2006 | North et al. | |
| 7,191,014 B2 | 3/2007 | Kobayashi et al. | |
| 7,216,000 B2 | 5/2007 | Sieracki et al. | |
| 7,228,179 B2 | 6/2007 | Campen et al. | |
| 7,239,916 B2 | 7/2007 | Thompson et al. | |
| 7,254,445 B2 | 8/2007 | Law et al. | |
| 7,266,412 B2 | 9/2007 | Stypulkowski | |
| 2003/0212439 A1 | 11/2003 | Schuler et al. | |
| 2005/0021090 A1 | 1/2005 | Schuler et al. | |
| 2005/0251061 A1 | 11/2005 | Schuler et al. | |
| 2005/0261061 A1 | 11/2005 | Nguyen et al. | |
| 2005/0261601 A1 | 11/2005 | Schuler et al. | |
| 2005/0261747 A1 | 11/2005 | Schuler et al. | |
| 2005/0288732 A1 * | 12/2005 | Schuler et al. | 607/48 |
| 2006/0155340 A1 | 7/2006 | Schuler et al. | |
| 2006/0206169 A1 | 9/2006 | Schuler | |
| 2006/0224189 A1 | 10/2006 | Schuler et al. | |
| 2007/0191887 A1 | 8/2007 | Schuler et al. | |
| 2007/0203532 A1 | 8/2007 | Tass et al. | |

FOREIGN PATENT DOCUMENTS

| | | |
|---|---|---|
| WO | 9739797 | 10/1997 |
| WO | 2006113305 | 10/2006 |

* cited by examiner

SYSTEMS AND METHODS FOR NEUROMODULATION USING PRE-RECORDED WAVEFORMS

RELATED APPLICATIONS

This application is a continuation-in-part of U.S. patent application Ser. No. 11/522,029 entitled "SYSTEM AND METHOD FOR PROVIDING A WAVEFORM FOR STIMULATING BIOLOGICAL TISSUE" filed on Sep. 15, 2006, now U.S. Pat. No. 7,715,912, which is a continuation-in-part of U.S. patent application Ser. No. 11/404,006, which was filed on Apr. 13, 2006, and entitled "SYSTEM AND METHOD FOR PROVIDING A WAVEFORM FOR STIMULATING BIOLOGICAL TISSUE," which claims the benefit of U.S. Provisional Patent Application No. 60/671,011, which was filed Apr. 13, 2005, and entitled "SYSTEM AND METHOD FOR PROVIDING A WAVEFORM FOR STIMULATING BIOLOGICAL TISSUE." Each of the above-identified patent applications is incorporated herein by reference.

TECHNICAL FIELD

The present invention relates generally to neuromodulation using electrical stimulation.

BACKGROUND

Various types of stimulators have been developed for a variety of in-vivo applications. For example, a stimulator can be employed for performing spinal cord stimulation, deep-brain stimulation or for stimulation of other neurological paths, such as for treatment of various disorders and diseases. Typically, each stimulator includes a waveform generator that generates its own waveform. For instance, a user defines the necessary parameters and the stimulator constructs the waveform accordingly. Usually the parameters include amplitude, frequency, phase symmetry and duty cycle. The more complex the waveform, the more parameters are necessary to describe the waveform. Implantable stimulators are constrained by space and typically cannot accommodate complex circuitry. Implantable stimulators, therefore, usually trade off waveform complexity for saving space. Thus, there is a need for alternate designs for a stimulator capable of generating waveforms to be used in neuromodulation.

SUMMARY

In one aspect, the present invention provides a method for neuromodulation to treat paralysis or weakness due to a cortical injury, comprising: recording an input waveform from a first site in the nervous system in a first subject, wherein the first site is selected from the group consisting of: motor cortex, premotor cortex, thalamus, red nucleus, olivary nucleus, and dentate nucleus; and applying an output waveform to a second site in the nervous system in a second subject, wherein the second site is selected from the group consisting of: motor cortex, premotor cortex, thalamus, red nucleus, olivary nucleus, and dentate nucleus; wherein the output waveform is identical to the input waveform or derived from the input waveform.

In another aspect, the present invention provides a neurostimulation system comprising: memory that stores waveform data for at least one waveform; a playback system that provides an output waveform based on the waveform data in the memory; a sensor for sensing a bodily activity; and a controller in communication with the sensor, wherein, in response to the bodily activity sensed, the controller controls the output waveform.

DETAILED DESCRIPTION

Figure 1:
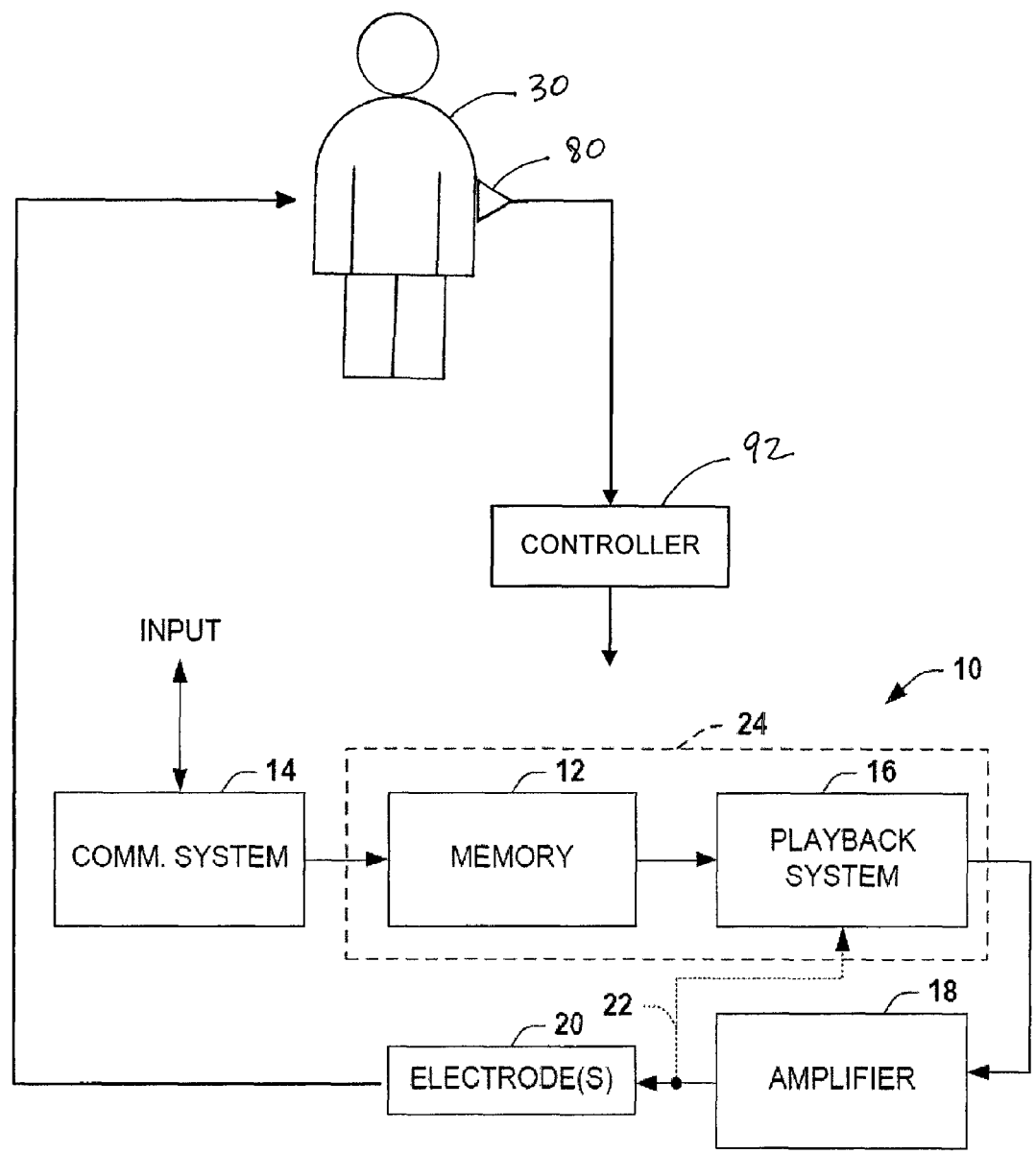
FIG. 1 depicts a block diagram of an embodiment of a programmable stimulation system that can be implemented according to an aspect of the present invention.

The present invention provides systems and methods for neuromodulation using waveform signals. As used herein, the term "waveform" describes the amplitude versus time relationship for a signal and may encompass one or more periods of a given signal. The waveform can be a recorded signal (which can be sampled and stored) or the waveform can be generated by a waveform generating device (e.g., an oscillator or other waveform generator). For example, the waveform generator can construct or derive the waveform from a mathematical formula or based on a drawing or other visualization of a waveform that may be displayed on a screen. As used herein, the term "waveform" is also intended to include neuro-electrical coding for communication (e.g., the sequence, timing, pattern, or frequency of neural firings). The waveform data in the memory can be preprogrammed, such as prior to implantation, or the waveform data can be programmed post-implantation of the system.

In one aspect, the present invention provides methods of neuromodulation using waveform signals. In certain embodiments, the method comprises recording an input waveform from a signal source site and applying an output waveform to a target site. In some instances, the input waveforms are obtained by recording an actual signal generated by a signal source site in a human or animal body. The signal source site may be any part of the nervous system, including the central nervous system and peripheral nervous system (including the innervations at the end organs).

These neural electrical signals may be known to control and/or regulate various body systems, including the nervous system, musculoskeletal system, endocrine system, immune system, pulmonary system, cardiovascular system, gastrointestinal system, or genitourinary system. As such, the recorded input waveforms may be associated with controlling and/or regulating certain bodily activity.

In some instances, the input waveform recordings are obtained from a site in the brain. Various parts of the brain may be the signal source site, such as the brain stem, cerebral cortex, subcortical cerebral structures, cerebellum including the deep cerebellar nuclei, basal ganglia, dentate, thalamus, or any component of the dentato-thalamo-cortical pathway. In some cases, the recordings are obtained from the motor cortex, premotor cortex, thalamus, red nucleus, olivary nucleus, or dentate nucleus.

The input waveform recordings may be obtained from various human and non-human source subjects. In some instances, the source subject is the same as the target subject (i.e., the subject who is receiving the neurostimulation). In such cases, the recording may be obtained from a portion of the target subject's nervous system that is healthy or at least partially functional. For example, where one part of the target subject's brain is diseased (e.g., due to a stroke), the recording may be obtained from the corresponding contralateral brain structure that is not affected by the disease. In other instances, the source subject and target subject are not the same. For example, the target subject may be a person, while the source subject may be another person or an animal, such as a non-human primate.

The input waveform recordings may be obtained from the source subject in various settings. In some instances, the input waveforms are recorded from the source subject while undergoing surgery, such as brain surgery, spinal surgery, or peripheral nerve surgery. The source subject may be conscious, sedated, or under anesthesia during the surgery. In other instances, the input waveforms are recorded from the source subject while at rest or while performing an activity or task. Such tasks include forelimb (upper extremity) tasks and hindlimb (lower extremity) tasks. For example, forelimb tasks include reaching, grabbing, picking with opposable thumbs, and grip squeezing; and hindlimb tasks include walking. In some cases, a plurality of recordings are made to form a library of waveform recordings, with each recording associated with a specific task, disease, or condition.

An output waveform is obtained based on the input waveform. The output waveform may be identical to the input waveform or a modification of the input waveform. The input waveform may be modified in various ways to produce the output waveform. For example, the input waveforms may be modified to have a different pattern, intensity, amplitude, frequency, duration, pulse width, or number of pulse trains. In another example, additional pulses may be added to the input waveform. The additional pulses may be added within the waveform or between waveforms. The additional pulses may be at pre-determined positions in the input waveform, at pre-determined intervals, or triggered by a spike in the input waveform. In another example, the input waveforms may be modified by copying, cutting, pasting, deleting, cropping, appending, or inserting desired segments of waveforms. In another example, the output waveform may be a composite of a plurality of input waveforms, which can be obtained from different signal source sites, different source subjects, or different time points at the same signal source site.

The output waveform can be applied as neurostimulation to any of various target sites in a target subject's body. The target site may be any part of the nervous system, including the central nervous system and the peripheral nervous system. In some instances, the target site is a structure in the brain. For example, the output waveform may be applied to the brain stem, cerebral cortex, subcortical cerebral structures, cerebellum including the deep cerebellar nuclei, basal ganglia, dentate, thalamus, or any component of the dentato-thalamo-cortical pathway. In some cases, the target site is the motor cortex, premotor cortex, thalamus, red nucleus, olivary nucleus, or dentate nucleus.

In some instances, the nervous system structure representing the target site anatomically corresponds to the nervous system structure representing the signal source site. For example, the input waveform recording can be obtained for one thalamus in one person and the output waveform can be applied to another thalamus in another person. In other instances, the nervous system structure representing the target site is different from the nervous system structure representing the signal source site. The target site may be neurologically proximal or distal to the signal source site; or, where the source subject and target subject are different, the target site may anatomically correspond to a structure that is neurologically distal to the signal source site. For example, an input waveform recording can be made in a thalamus and the output waveform can be applied to a cerebral cortex. In another example, an input waveform recording can be made in a cerebral cortex and the output waveform can be applied to a cerebellum. In another example, an input waveform recording can be made in a cranial nerve nuclei and the output waveform can be applied to the cranial nerve itself.

The output waveform may be applied as neurostimulation using any of various conventional means. In some cases, the stimulation is applied by direct conduction. For example, the stimulation can be performed with an electrode positioned at the target site. The electrode can be implanted permanently, chronically, or temporarily. In other cases, the stimulation is applied externally or without direct contact with the target site structure. For example, the neurostimulation may be performed using a probe that transmits electromagnetic energy (e.g., RF) that is captured by the target site.

In some instances, the neurostimulation is applied while the target subject is performing a task. A neurostimulation waveform is selected based on the task that is being performed. Without intending to be bound by theory, it is believed that applying neurostimulation in this manner will facilitate rehabilitation by enhancing the natural process of neural plasticity.

In certain embodiments, the method includes a process for providing physiologic feedback regulation. In some instances, the method further comprises sensing a bodily activity in the target subject. The bodily activity to be sensed by the sensor is any characteristic or function of the body including bodily organs, such as mechanical, motion, electrical, or chemical activity and includes, for example, gastrointestinal function including gastric acid, intestinal motility, and peristalsis; temperature; respiratory function; heart rate; capillary pressure; venous pressure; perfusion; blood gases such as carbon dioxide including partial pressure of carbon dioxide; oxygenation including blood oxygenation levels, oxygen saturation levels partial pressure of oxygen, oxygen consumption, oxygen pressure; water pressure; nitrogen pressure; carbon dioxide pressure in the tissue; circulation (including blood and lymphatic); electrolyte levels in the circulation/tissue; diffusion or metabolism of various agents and molecules (such as glucose); neurotransmitter levels; body temperature regulation; blood pressure; blood viscosity; metabolic activity; cerebral blood flow; pH levels; vital signs; galvanic skin responses; perspiration; electrocardiogram; electroencephalogram; action potential conduction; chemical production; body movement including limb movement, posture, and gait; response to external stimulation; cognitive activity; dizziness; pain; flushing; motor activity including muscle tone; visual activity; speech; balance; diaphragmatic movement; chest wall expansion; concentration of certain biological molecules/substances in the body such as, for example, glucose, liver enzymes, electrolytes, hormones, creatinine, medications, concentration of various cells, platelets, or bacteria. These bodily activities can be measured utilizing a variety of methods including but not limited to chemical analysis, mechanical measurements, motion sensors, laser, and fiber-optic analysis.

In response to the bodily activity sensed, the output waveform can be initiated or adjusted to affect the bodily activity. For example, the bodily activity being sensed may be gastric pH levels. In response to the gastric pH level, the output waveform can be initiated or adjusted to affect the gastric pH production. In another example, the bodily activity being sensed may be heart rate. In response to an abnormal heart rate, the output waveform can be initiated or adjusted to affect the heart rate. In another example, the bodily activity being sensed may be limb motion. In response to a tremor in the limb, the output waveform can be initiated or adjusted to reduce the tremor.

Various types of adjustments can be made to the output waveform. For example, the waveforms may be modified to have a different pattern, intensity, amplitude, frequency, duration, pulse width, or number of pulse trains. In another example, additional pulses may be added to the waveform. The additional pulses may be added within the waveform or between waveforms. The additional pulses may be at pre-determined positions in the waveform, at pre-determined intervals, or triggered by a spike in the waveform. In another example, the waveforms may be modified by copying, cutting, pasting, deleting, cropping, appending, or inserting desired segments of waveforms. In another example, the neurostimulation may be adjusted by selecting another waveform from a library of waveforms.

The present invention can be used to treat a variety of conditions or disorders. Non-limiting examples of medical conditions that can be treated according to the present invention include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, inflammatory medical conditions or any suitable combination thereof. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, abnormal malformational causes or suitable combinations thereof.

With respect to treating neurological medical conditions, such medical conditions can involve any medical conditions related to the components of the nervous system such as, for example, the brain including the cerebellum, brain stem, pons, midbrain, medulla; the spinal cord; peripheral nerves; peripheral ganglia; and nerve plexuses. Non-limiting examples of neurological conditions include neurodegenerative disorders, Alzheimer's disease, epilepsy, multiple sclerosis, ALS, Guillan Barre, neurovascular disorders including stroke, cerebral palsy, intracerebral hemorrhage, dementia, vertigo, tinnitus, diplopia, cerebral vasospasm, aneurysm, atriovenous malformation, brain malformations, movement disorders, multi-system atrophy, olivopontocerebellar degeneration, familial tremor dystonia including cervical dystonia, torticollis, facial dystonia, blepharospasms, spasmodic dysphonia, radiculopathy, neuropathic pain, sleep disorders, disorders of temperature regulation in the body and extremities, postherpetic neuralgia involving the face, head, body or extremities. The neuropathic pain may be caused by fracture, crush injury, compressive injury, repetitive movement injury, diabetes, trauma, alcohol, infection, or hereditary. The sleep disorder may be sleep apnea, restless leg syndrome, narcolepsy, snoring, insomnia, drowsiness, or suitable combinations thereof.

Non-limiting examples of movement disorder include or manifest as: ataxia, akinesia, athetosis, ballismus, hemiballismus, bradykinesia, dystonia, chorea including Huntington's disease, multiple system atrophies (e.g., Shy-Drager syndrome), myoclonus, Parkinson's disease, progressive supranuclear palsy, restless leg syndrome and periodic limb movement disorder, tics, Tourette's syndrome, tremor (e.g., essential tremor, resting tremor), Wilson disease, tardive dyskinesia, and paralysis or weakness due to stroke or other cortical injury.

In another aspect, the present invention provides a stimulation system for neuromodulation using waveform signals. Turning to the figures, FIG. 1 depicts a stimulation system 10 that can be implemented according to an aspect of the present invention. The stimulation system 10 includes memory 12 that stores (or records) waveform data corresponding to one or more waveforms. The waveform data can be stored in the memory 12 based on an INPUT signal received by a communication system 14. The one or more waveforms can be stored as one or more complete periods of the waveform, which can be referred to as snippets. As described herein, the waveform data that is stored in the memory 12 corresponds to one or more actual waveforms, which can be an analog or digital representation of the waveform(s). This type of waveform data that is stored in the memory 12 thus is referred to herein as non-parametric waveform data.

The communication system 14 can include a receiver that receives the INPUT signal via one or more communication modes, such as including radio frequency (RF), infrared (IR), direct contact (e.g., electrically or optically conductive path), capacitive coupling, and inductive coupling to name a few. The INPUT signal further can be provided via more than one communication mode, such as providing the INPUT signal as including one or more waveforms via one mode and command information (e.g., scheduling and programming information) via another mode. The communication system 14 can be capable of bi-directional communications, such as also including a transmitter or transceiver circuitry. The transmitter and receiver portions of the communication system 14 can employ the same or different communication modes.

The memory 12 can be implemented as an analog memory, such as is capable of storing an analog version of the waveform that is received by the communication system 14. The memory can also be implemented as digital memory that stores a digital representation or sample of the input waveform or stores a digitally encoded version of the waveform. For instance, the memory 12 can store the sample waveform as a digital sample, such as using pulse code modulation (PCM) or adaptive differential pulse code modulation (AD-PCM) or pulse width modulation (PWM), although other modulation techniques can be utilized. The digital sample of the waveform further may be stored in a compressed format according to one or more CODECs (e.g., MP3, AAC, 3GPP, WAV, etc.), although compression is not required. There are a multitude of varying standards that can be grouped in three major forms of audio CODECs, including, for example, direct audio coding, perceptual audio coding, and synthesis coding, any one or more of which can be employed to store a digital representation of waveforms in the memory 12.

A playback system 16 is configured to retrieve and play back one or more waveforms according to selected waveform data stored in the memory 12. The playback system 16 can be implemented as hardware (e.g., one or more integrated circuits), software or a combination or hardware and software.

The implementation of the playback system 16 can vary, for example, according to the type of audio (analog or digital) that is stored in the memory 12. The playback system 16, for example, can be programmed with one or more audio CODECs that convert (or decode) the encoded waveform data into a corresponding output waveform.

The playback system 16 can be implemented as an integrated circuit 24, such as including a microcontroller or microprocessor. For instance, suitable microcontroller integrated circuits (ICs) are commercially available from Atmel Corporation of San Jose, Calif. Such microcontroller ICs may include the memory 12 integrated into the IC 24, such as in the form or FLASH memory or other programmable memory (electrically programmable read only memory (EPROM)), or the memory 12 can be external to the IC 24.

The playback system 16 provides the output waveform to an amplifier 18 that amplifies the output waveform. The playback system 16 further can be configured to provide output waveforms to one or more output channels, each output channel providing an amplified output waveform corresponding to the waveform data stored in the memory 12. One or more electrodes 20 can be coupled to each of the channels for delivering electrical stimulation to biological tissue located adjacent the electrode(s).

As an example, the playback system 16 can be configured to select one or more waveforms from the memory 12 for providing a corresponding output waveform. As mentioned above, a plurality of different types of waveforms can be stored in the memory 12, generally limited only by the size of the memory. The playback system 16 thus can select and arrange one or more waveforms to provide a desired output waveform pattern. Additionally, the playback system 16 further can combine a plurality of different waveforms into more complex composite output waveforms. It will be appreciated that the ability of selecting from a plurality of predefined stored waveforms affords the stimulation system enhanced capabilities, as virtually any output waveform can be stored and played back from the memory 12.

The design can be simplified even further by storing waveforms of gradually changing parameters in the memory 12. For example, a plurality of versions of the same waveform, but of varying amplitude, can be stored in the memory 12 so as to effectively eliminate the need for additional amplitude controlling circuitry. Accordingly, if a greater or lesser amplitude may be required for a given application, an appropriate different waveform can be selected. The playback system 16 can also be programmed and/or configured to manipulate one or more selected waveforms from the memory 12, such as using digital or analog computation, to vary parameters (e.g., amplitude, frequency, phase symmetry and/or duty cycle) of the one or more selected waveforms. The corresponding amplified output signal corresponds to an amplified version of the selected waveform, including any such manipulations.

The amplifier 18 can be implemented as an analog amplifier or a digital amplifier. For an analog version of the amplifier 18, a digital-to-analog converter (not shown) can provide a corresponding analog version of the output waveform and a linear amplifier, in turn, can operate to amplify the analog output waveform to a desired level. Power conditioning circuitry can be utilized to provide a desired potential for use in generating the amplified output waveform. Alternatively, the amplifier can be implemented as a class D amplifier (or switched power supply), although other amplifier topologies can also be used. By implementing the amplifier as a class D amplifier, the amplifier 18 can run directly off a battery or other power supply efficiently and be implemented using low-voltage components. Those skilled in the art will appreciate various types of switching amplifier topologies are that can be utilized in the system 10. Additionally, the amplifier 18 can be configured to operate in a current mode or a voltage mode control, such as to provide a desired current or voltage.

The amplifier 18 can comprise a network of amplifiers arranged to drive a plurality of loads (depicted as electrodes 20) according to respective output waveforms provided by the playback system 16. The electrode(s) 20 can be implanted in strategic locations in the body of subject 30 according to given application of the stimulation system 10. For example, the electrode(s) can be located within the brain, spinal cord or other anatomic locations. The anatomic locations can be in close proximity to the playback system or at remote locations.

The system 10 can be implemented as an open loop system or a closed loop system. For the example of a closed loop system, the system 10 can also include feedback, indicated as dotted line 22. The feedback 22 provides information about the stimulus being applied to the electrode(s) and/or about a characteristic of the electrode(s). As an example, the feedback 22 can provide an electrical signal to the playback system 16, based on which an indication of load impedance associated with the electrode(s) can be determined.

The impedance characteristics can be utilized for a variety of purposes. For instance, the impedance can be employed to implement current control, such as by the playback system 16 selecting a predefined waveform from the memory 12 to maintain a desired current level in the waveform that is provided to the electrode(s) 20. Alternatively or additionally, the impedance characteristics can be used as part of diagnostics, such as by recording (or logging) impedance over extended periods of time and evaluating a condition of the electrode(s). As another alternative, the feedback 22 can be employed to ascertain high impedance conditions (e.g., an open circuit) or a low impedance condition (e.g., a short circuit). Those skilled in the art will understand and appreciate various approaches that can be implemented to provide the feedback 22. Additionally, various types of diagnostic or operational controls can be implemented based on such feedback.

Since the waveform is played back from non-parametric waveform data that is stored in the memory 12, the system 10 can be implemented in a cost efficient manner from commercially available recording and playback circuitry. Additionally, because the waveforms can be generated externally, provided to the system 10, and stored in the memory 12, there is a greater degree of flexibility in the types and complexity of waveforms that can be stored in the memory. That is, the system 10 is not constrained by limitations in the cost or size or complexity of a typical parametric waveform generator. Additionally, the playback system 16 may further construct more complex waveforms by combining two or more stored waveforms in a particular order (e.g., a pattern of waveform trains). As an example, one or more of the waveforms stored in the memory can include actual recorded impulses (electrical waveforms), such as can be recorded from the patient in which the stimulation system 10 is to be implanted, from a different person or from a non-human animal subject. The playback system 16 can also combine two more waveforms by performing a superimposition of such waveforms to construct a desired aggregate waveform.

In certain embodiments, stimulation system 10 further includes a sensor 80 to provide physiologic feedback regulation. Sensor 80 is located on or within the body of subject 30 and detects mechanical, motion, electrical, and/or chemical activity. Sensor 80 may be located within the target site, proximal to the target site, or distal to the target site, whether in or outside the nervous system. Examples of electrical activity that can be detected by sensor 80 include neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, sensor 80 can measure, at any signaling stage, neuronal activity of any of the extensive connections of the target site. In particular, sensor 80 may detect the rate and pattern of the neuronal electrical activity to determine the electrical signal to be provided to the lead. Examples of chemical activity detected by sensor 80 located within or proximal to the target site include measurements of neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the target sites or communicate with the target sites. With respect to detecting electrical or chemical activity in the nervous system, sensor 80 could be placed in the brain, the spinal cord, cranial nerves, and/or spinal nerves. For example, sensor 80 could be placed in the intralaminar nuclei to sense neuronal electrical activity. In certain embodiments relating to treating movement disorders, the activity in the intralaminar nuclei is sensed. Sensor 80 placed in the brain is preferably placed in a layer-wise manner. For example, sensor 80 could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. Sensor 80 could measure the same types of chemical and/or electrical activity within or proximal to the target site as described above. With respect to detecting mechanical, motion, electrical, or chemical activity by sensor 80 located outside the nervous system, sensor 80 may be placed in venous structures and various organs or tissues of other body systems, such as the endocrine system, musculoskeletal system, respiratory system, circulatory system, urinary system, integumentary system, and digestive system or such sensors may detect signals from these various body systems. For example, sensor 80 may be an external sensor such as a pulse oximeter, or an external blood pressure, heart, and respiratory rate detector. In another example, sensor 80 may be motion detectors attached to a body limb for detecting tremors, abnormal gait, or other abnormal movement. All the above-mentioned sensing systems may be employed together or any combination of less than all sensors may be employed together.

Sensor 80 sends a sensor signal conveying information about the bodily activity to stimulation system 10. In response to the sensor signal, stimulation system 10 initiates or adjusts the application of the waveform neurostimulation to the target site to affect the bodily activity. In certain embodiments, the signal from sensor 80 is in communication with a controller 92, which receives the signal and controls the output of neurostimulation to the target site. The signal from sensor 80 may be transmitted via a transmission line (e.g., an electrical or optical connection) or via wireless communication (e.g., radio-frequency, infrared, or ultrasound). Controller 92 may be in communication with and control various components of system 10 to initiate or adjust the neurostimulation applied by electrode 20. For example, controller 92 may control communication system 14, memory 12, playback system 16, and/or integrated circuit 24. In the embodiment of FIG. 1, controller 92 is internal to the body of subject 30. However, in alternate embodiments, controller 92 is external to the body of subject 30.

Figure 2:
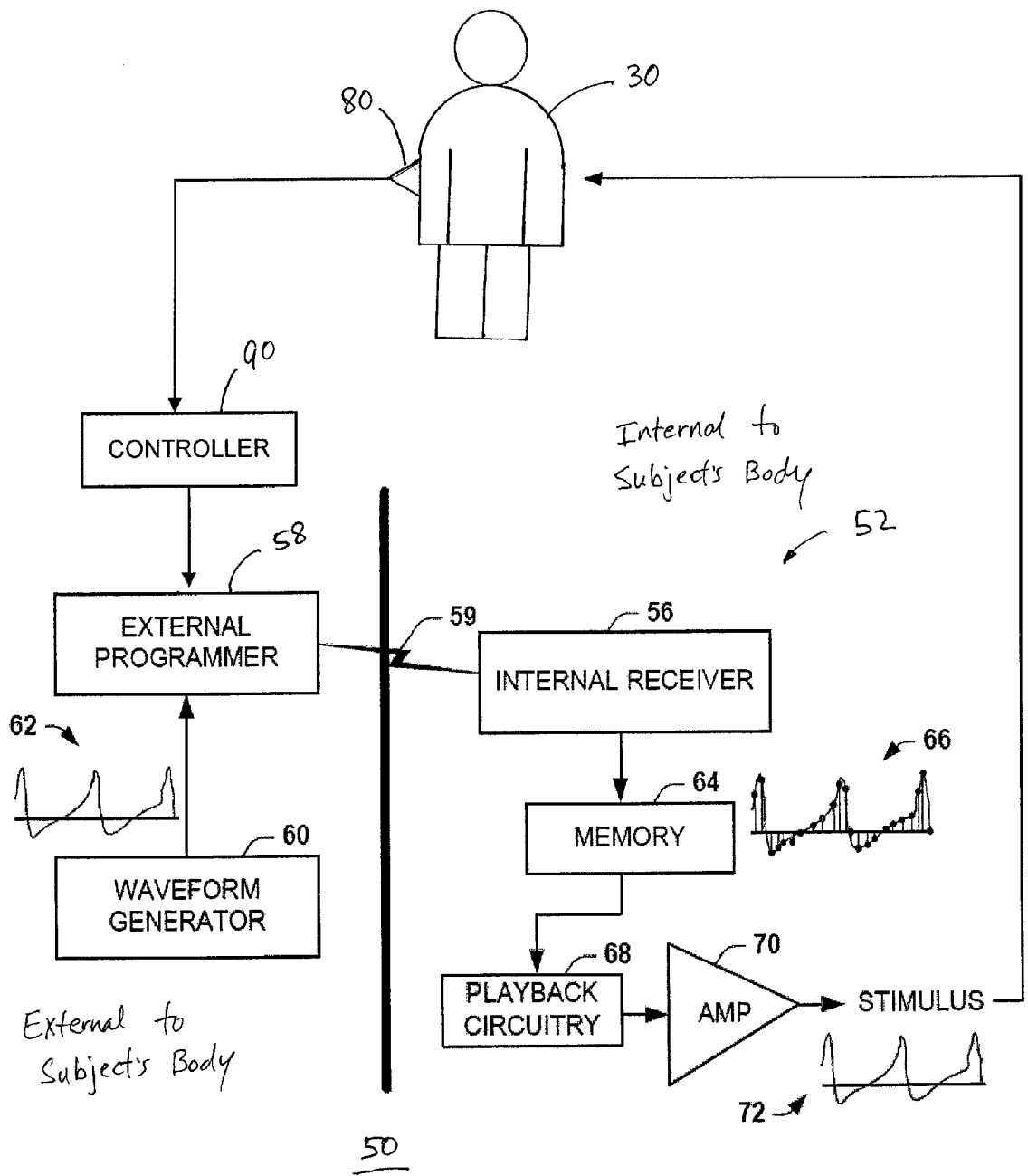
FIG. 2 depicts an example of yet another stimulation system that can be implemented according to an aspect of the present invention.

FIG. 2 depicts an example of a programmable stimulation system 50 that can be implemented according to an aspect of the present invention. The system 50 comprises an implantable pulse generator (IPG) 52 that is implanted in the body of a subject 30. The IPG 52 can be implanted in various locations, such as under the skin of the chest (e.g., below the collarbone) or other anatomic location. In contrast to many existing IPG designs, the IPG 52 is not required to generate a pulse or waveform, but instead is configured to play back one or more predefined waveforms. The IPG 52 includes an internal receiver 56 that can receive a signal from an external programmer 58, which is located external to the body of subject 30. The external programmer 58 can communicate the signal to the receiver 56 using one or more communications modes, such as described herein. In the example, of FIG. 2, a connectionless communications mode is illustrated, although a physical connection can be made to provide an electrical or optical conductive medium for data communications.

A waveform generator 60 can provide one or more waveforms 62 to the external programmer 58 for transmission to the IPG 52. The waveform generator 60 can include any type of device or system that can generate the one or more waveforms 62, including a programmable signal generator, a pulse generator, and a waveform synthesizer to name a few. The waveform generator 60 further may be a PC-based system or a stand alone system capable of generating one or more desired waveforms. The waveform generator 60 can also be programmed with biological, recorded waveforms, such as may have been measured and recorded from the body of subject 30 or from any other biological subject (e.g., human or other animal).

For electrical stimulation of a patient's brain, the waveform can be recorded as electrical impulses measured from one or more anatomical regions of a biological subject's brain. The waveform generator 60 thus can provide the biological, recorded waveforms to the external programmer 58 for transferring such waveforms to the memory via the internal receiver 56 of the IPG 52. The measurements, for example, can be made by sensing electrodes inserted within target tissue or by external sensors placed adjacent target tissue or a combination of internal or external sensors. Those skilled in the art will understand and appreciate various types of sensors and measurement devices that can be employed to measure and record the biological waveforms. Additionally, while the foregoing mentions recording electrical impulses from one or more regions of a subject's brain, it is to be appreciated that the impulses can be recorded from other nerve tissue, one or more other organs, or other anatomical sites (human or other animal) or any combination thereof.

The external programmer 58 transmits a signal 59 to the receiver 56 of the IPG 52 corresponding to the waveform 62 provided by the generator 60. As discussed herein, the signal 59 transmitted by the external programmer 58 can include (or encode) the actual waveform 62 provided by the waveform generator 60 (e.g., an actual biological, recorded waveform or a synthesized waveform). The external programmer can transmit the signal 59 as including a complete period, more than one period (e.g., snippets) or as a fraction of a period of the desired waveform 62 in any communications mode. The receiver 56, for example, can provide the waveform to the memory as encoded waveform data, such as corresponding to an encoding scheme implemented by the waveform generator 60. Alternatively, the receiver 56 can demodulate/decode an encoded received signal and provide a corresponding demodulated/decoded signal 66 to the memory 64 so that the waveform data corresponds to the one or more waveforms 62. Additionally encoding may also be performed by the receiver 56 or other circuitry (not shown) for providing encoded waveform data for storing the waveform(s) 62 the memory 64.

The sample of the waveform 66 stored in the memory 64 can correspond to an analog version of the waveform or a corresponding digital (e.g., PCM) representation of the waveform. Those skilled in the art will appreciate various different representations that can be stored in the memory 64 based on the teachings contained herein. It will further be understood that some or all of the waveforms 66 stored in the memory 64 can be programmed prior to implantation of the IPG 52 within the body of subject 30.

After a desired number of one or more waveforms 66 have been stored in the memory 64, such as during a program mode, playback circuitry 68 can play back one or more selected waveforms 66 from the memory 64. The playback circuitry 68 can play back a waveform according to a defined play back schedule, which may be a periodic or continuous schedule. Alternatively or additionally, the playback circuitry 68 can be configured to play back one or more selected waveforms in response to a stimulus, which stimulus can be user-generated or provided by associated sensing circuitry (not shown).

The playback circuitry 68 can play back the one or more selected waveforms by retrieving the selected waveform(s) from the memory and providing the output waveform(s) to one or more amplifiers 70. The amplifier 70 amplifies the output waveform to a desired level to provide a corresponding amplified version of the waveform. That is, the amplified waveform 72 can be substantially the same as the waveform 62 generated by the waveform generator 60. Alternatively, when the waveform 62 is stored as encoded data, the amplified waveform 72 can correspond to a decoded version of the waveform. Typically, a plurality of waveforms 66 are stored in the memory 64 to provide a greater selection of available waveforms for operating the IPG 52. The amplified waveform 72 can be provided to one or more strategically placed electrodes or other implantable devices capable of delivering an electrical stimulus to adjacent biological tissue.

In certain embodiments, stimulation system 50 further comprises a sensor 80 to provide physiologic feedback regulation. In the embodiment shown in FIG. 2, sensor 80 is in communication with a controller 90 that is external to the body of subject 30. Controller 90 is in communication with and controls external programmer 58 to initiate or adjust the neurostimulation. In alternate embodiments, controller 90 is internal to the body of subject 30 and/or controls other components of stimulation system 50.

Figure 3:
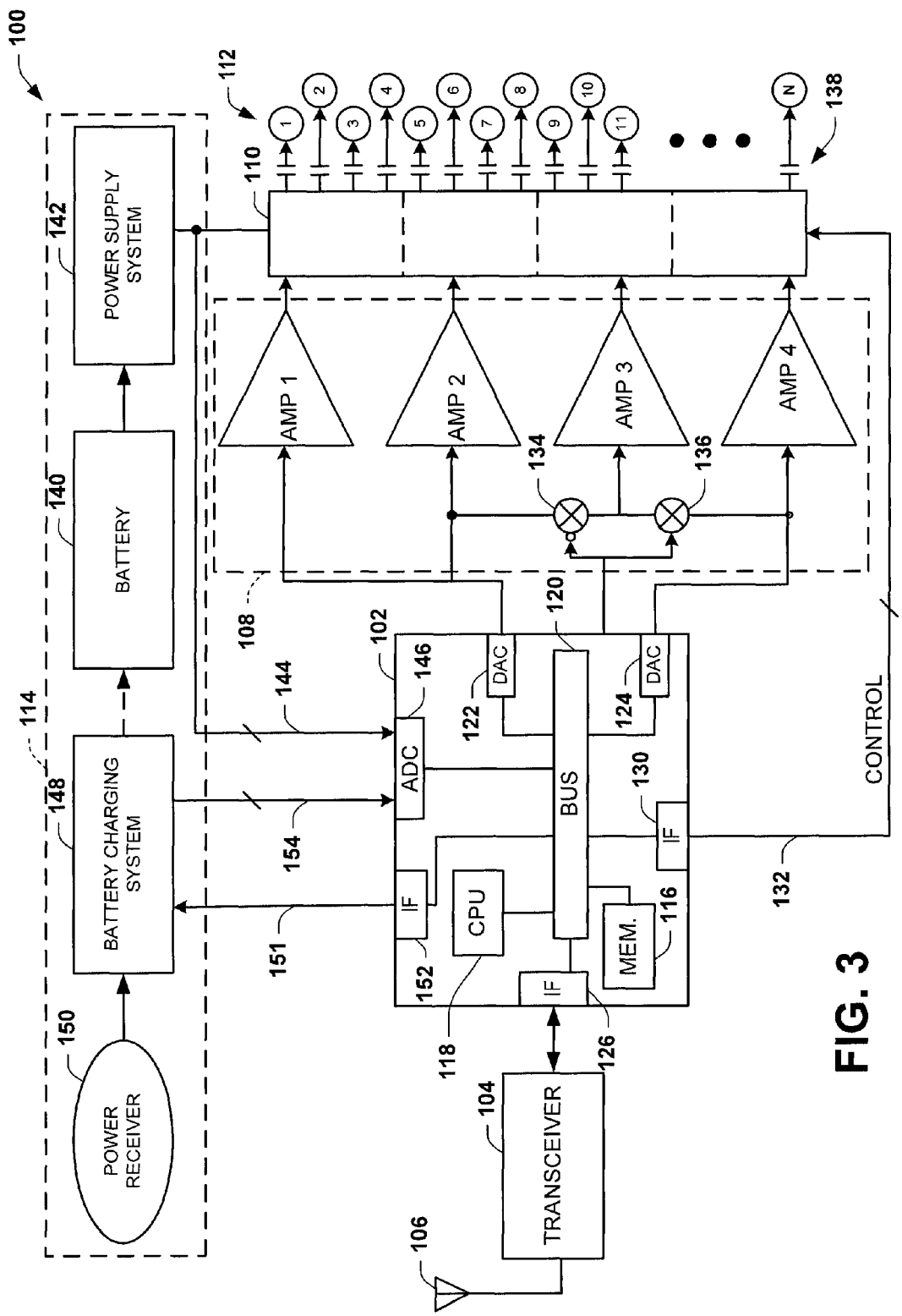
FIG. 3 depicts a block diagram of an embodiment of an implantable pulse generator system that can be implemented according to an aspect of the present invention.

FIG. 3 depicts an example of another implantable pulse generator (IPG) system 100 that can be implemented according to an aspect of the present invention. The IPG system 100 is configured to deliver electrical stimulation to target tissue, such as by using one or more electrodes. In the example of FIG. 3, IPG the system 100 includes a control system 102 that is operative to control recording and playback of one or more waveforms for implementing electrical stimulation. The control system 102 can be implemented as a microcontroller unit (e.g., an integrated circuit) or as a combination of one or more integrated circuits that can be programmed and/or configured to implement the functions described herein.

The control system 102 is coupled to a transceiver 104. The transceiver 104 can be coupled to an antenna 106 for implementing wireless communications to and from the IPG system 100. As used herein, the term "wireless" refers to communication of information without a physical connection for the communication medium (the physical connection usually being electrically conductive or optical fiber). As described herein, the transceiver 104 alternatively could be implemented as a hard wired connection (e.g., electrically conductive or optical links). Those skilled in the art will understand and appreciate various types of wireless communication modes that can be implemented by the transceiver 104, such as described herein. As an example, the transceiver 104 can be programmed and/or configured to implement a short range bi-directional wireless communication technology, such as Bluetooth or one of the 802.11x protocols.

The transceiver 104 can also employ security features to inhibit unintentional or unauthorized access to the IPG 100. The security features can be implemented as software and/or hardware, such may be part of the transceiver and/or as part of the control system 102. As one example, the security measures can be integrated as part of the wireless protocol implemented by the transceiver 104 (e.g., Bluetooth wireless communications employs the SAFER+ algorithm for authentication and key generation). Other communication protocols may employ different security measures to mitigate unauthorized communication with the IPG. Alternatively or additionally, the transceiver 104 can utilize a predefined key or ID associated with the IPG 100 to identify the intended recipient of the communication and confirm the received information as originating from an authorized or trusted source.

The control system 102 is connected to provide one or more output waveforms to an amplifier system 108. The amplifier system 108 is connected to receive and amplify the output waveforms from the control system 102 and provide the corresponding amplified waveforms to an output system 110. The output system 110 is configured to distribute the amplified waveforms to a set of one or more corresponding output channels 112. The output channels 112 may include output ports electrically coupled directly with respective electrodes or other peripheral devices coupled to receive the output waveforms from the IPG system 100. The IPG system 100 can also include a power system 114 that is operative to supply power for operation of the various components.

Turning to the contents of the control system 102, the control system 102 includes memory 116 that can store digital data representing each of the one or more waveforms. The memory 116 can be implemented as random access memory (RAM), flash memory, programmable read-only memory (PROM), electrically erasable programmable read-only memory (EEPROM) or other types of memory capable of storing digital representations of the one or more waveforms. The storage capacity of the memory 116 may vary according to application design requirements of the IPG 100.

A central processing unit (CPU) 118 is coupled to the memory 116, such as via a bus 120. The bus 120 can be any type of connection or backplane (or a combination thereof) that enables communication between the various components of the control system 102, including the memory 116 and the CPU 118. For example, the CPU 118 and memory 116 can be instantiated on an integrated circuit, such as a microcontroller or application specific integrated circuit (ASIC) that forms the control system 102. In such an embodiment, the bus 120 can be implemented as an internal IC bus. While the memory 116 is depicted as residing within the control system 102, at least a portion of the memory could be implemented as an external memory structure (e.g., implemented as one or more integrated circuits).

The CPU 118 can selectively retrieve the respective waveforms from the memory 116 and supply (or play back) the selected retrieved waveform to the amplifier system 108. As an example, the CPU 118 can perform computer-executable control instructions that control which of the one or more waveforms are supplied to the amplifier system 108. The executable instructions can also control or adjust parameters of the output waveforms. The computer-executable control instructions can be stored in the memory 116, such as with the waveform data. The control system 102 can also include one or more digital-to-analog converters (DAC) 122 and 124 that are connected with the bus 120. The CPU 118 thus can supply the retrieved waveform data to the DACs 122 and 124. The DACs 122 and 124 can convert the stored digital waveforms to corresponding analog output waveforms and provide the analog output waveforms the amplifier system 108.

The CPU 118 can also employ computer executable instructions (such as may be stored in the memory 116) to control operation of the transceiver 104. The CPU 118 can communicate with the transceiver 104 through the bus 120 through a corresponding interface 126 that is connected between the transceiver and the bus. As an example, during a programming mode, the CPU 118 can receive and send information via the transceiver 104 for programming the memory 116. The information received, for example, may include more digital waveforms that are stored in the memory for play back during a normal operating mode.

The information received via the transceiver 104 can also include computer-executable instructions such as for control operating parameters of the IPG 100. Alternatively, some or all of the IPG operating parameters can be pre-programmed. The programmable operating parameters can include scaling parameters for adjusting one more parameters of the output waveform. For example, the scaling parameters can include the amplitude, pulse width, pulse duration, as well as control the number of pulse trains of the one or more stored waveforms that are supplied as the corresponding analog output waveform to the amplifier system 108. The CPU 118 can modify such scaling of parameters during operation to provide a modified version of the stored waveform (e.g., the modifications being based on feedback 144 to provide for closed loop operation).

The CPU 118 can also control which of the plurality of output channels 112 are provided with corresponding output waveforms. For example, the CPU 118 can provide a CONTROL (or selection) signal 132 to the output system 110 through the bus 120 and via a corresponding interface 130. The output system 110 can be implemented as a switching matrix or multiplexer that is configured to selectively couple selected corresponding output signals from the amplifier system 108 to the corresponding output channels 112 based on the CONTROL signal. For instance, the output system 110 can include network of switches that are configured to complete an electrically conductive path from the control system to the selected output channel(s). The output system 110 thus can selectively distribute output waveforms to one or more of the output channels 112 based upon the control instructions stored in the memory 116 that define how such distribution is to occur.

As described herein, an electrode (or electrodes) can be coupled to each of the corresponding output channels 112 for delivering corresponding electrical stimulus based on the amplified analog waveforms distributed to the corresponding outputs by the output system 110. The size and the configuration of the output system 110 can vary according to the number of output channels as well as the number of respective inputs provided by the amplifier system 108.

The amplifier system 108 can include a plurality of amplifiers, which in the example of FIG. 3 are depicted as including four amplifiers (indicated at AMP 1 through AMP 4). As mentioned above, the control system 102 includes DACs 122 and 124 that provide corresponding analog output waveform signals to the amplifier system 108. In the example of FIG. 3, the DAC 122 is coupled to supply a corresponding analog input two amplifiers AMP 1 and AMP 2. The DAC 124 is coupled to provide a corresponding output signal to the amplifier AMP 4. The control system 102 also provides the corresponding signal indicated at 132 for selecting which of the output waveforms is connected to supply the analog input to the amplifier AMP 3. For the example of FIG. 3, in which there are two analog outputs provided by the control system 102, the control system 102 can provide an output that controls operation of corresponding switches 134 and 136. The output thus can operate to connect the output of DAC 122 with the amplifier AMP 3 or to connect the output of DAC 124 with the input of AMP 3. Those skilled in the art will understand and appreciate various other types of circuits and switch networks that can be utilized to supply a desired output waveform selectively to the input of amplifier AMP 3. Such circuitry can also include an inverter to supply an inverted version of a stored waveform, for example.

To mitigate interference between the respective output channels 112, DC blocking capacitors 138 can be connected between the output system 110 and the corresponding ports of the output channels 112. The DC blocking capacitors 138 can be selected to have a corresponding capacitance based upon the desired frequency range at which the output signals are to be supplied to the corresponding output channels 112.

The power system 114 includes a battery 140 that stores a charge for providing corresponding DC voltage to the IPG system 100. For example, the battery 140 supplies the DC output voltage to an associated power supply system 142. The amount of voltage provided the battery 140 can vary according to the power requirements of the IPG system 100.

The power supply system 142 can also include load tracking and switch mode power supplies for providing appropriate power to the various parts of the IPG system. As an example, the load tracking aspect of the power supply system 142 can vary the voltage rails supplied to the output system 110 as a function of the particular output waveform(s) being provided by the control system 102 to the amplifier system 108.

Additionally or alternatively, the control system 102 can vary the voltage rails of the output system 110 according to IPG power requirements, such as by controlling the power supply system 142. The control system 102 can also vary the amplitude of the analog output waveform by controlling a variable gain of the respective amplifiers. Alternatively, as described herein, digital waveforms stored in the memory 116 can be preprogrammed with different desired amplitudes. Thus, to provide the desired amplitude at a given channel, the control system 102 can play back the given waveform that has the desired amplitude.

The output system 110 can also provide feedback, indicated at 144, to the control system 102. The feedback 144 can be sent over one or more connections depending on the extent of information being provided. In the example of FIG. 3, the feedback 144 can include a plurality of inputs, each being provided to the analog digital converter ADC 146. The CPU 118 can receive a corresponding digital representation of the feedback signals received ADC 146. For instance, the digital feedback information can be stored in memory 116 for use by one or more control functions that are being executed by the CPU 118.

The CPU 118 (running executable instructions) can evaluate the corresponding digital representation of the feedback signals to ascertain information about the operation of the IPG 100. As one example, the feedback 144 can provide an indication of the output impedance for the respective output channels (e.g., including the impedance of the electrodes connected at the respective output channels). The CPU 118 or other circuitry can determine the impedance, for example, as a function of the voltage or current signal provided by the feedback 144. The determined impedances can be used for a variety of functions.

By way of example, the control system 102 can implement safety functions based on the detected impedance at the respective output channels 112. For instance, if the digitally converted feedback information indicates a sufficiently low impedance (e.g., corresponding to a short circuit condition at one or more output channels 112) the CPU 118 can implement pre-programmed control procedures. Additionally, if the impedance information provided by the feedback 144 indicates a sufficiently high impedance (e.g., corresponding to an open circuit condition), suitable procedures may be implemented. A high impedance condition may indicate that an electrode has been decoupled from its output channel. During operation, in response to detecting an impedance that is outside normal operating parameters, the control system 102 can, for example, adjust and/or discontinue providing output waveforms to one or more of the output channels 112 at which the condition has been detected.

As another example, the feedback 144 can provide an indication of charge associated with the output channels. For example, the feedback 144 can include an indication of voltage and current characteristics for each of the output channels 112. The control system 102 can be programmed (e.g., with appropriate executable instructions stored in the memory 116) to compute a charge density value based on input parameters and known electrical characteristics of each output channel. If the computed charge density for a given output channel 112 exceeds a predetermined threshold, the control system 102 can deactivate the given output channel.

Still another example might be to program the control system 102 to perform charge balancing associated with operation of the amplifiers and/or the output system 110 based on the feedback 144. For example, the control system 102 can monitor the charge at a given output channel such as to help ensure that no net DC voltage exists in any of the channels 112 that might be adverse to the desired electrical stimulation being provided at each channel.

The control system 102 can also activate the transceiver 104 for transmitting appropriate information when the feedback 144 indicates these and other sensed conditions may reside outside of expected operating parameters. The control system 102 can initiate transmission of the information automatically in response to detecting operation outside of expected operating parameters. Alternatively, the control system 102 can store such information (e.g., in the memory 116) and transmit in response to being interrogated by a corresponding external transmitter or external transceiver.

The feedback 144 can also provide an indication of the available energy in the battery 140. Accordingly, one or more of the inputs in the feedback 144 can be converted to a corresponding digital representation and evaluated by the CPU 118. If the available battery power falls below a predetermined threshold, for example, appropriate action can be taken to conserve power or otherwise provide an indication (e.g., via the transceiver 104) that the battery 140 should be replaced or recharged.

The power system 114 can also include a battery charging system 148 and a power receiver 150. The battery charging system 148, for example, may include charging control circuitry for the battery 140 as well as a power converter (e.g., including a rectifier) that is operative to convert the power received by the power receiver 150 to an appropriate form and level to facilitate charging the battery 140. In this regard, the battery 140 can be a rechargeable type, such as a lithium battery, or nickel cadmium battery capable of extended use between charges. Alternatively, as described herein, the battery 140 may be replaceable.

The power receiver 150, for instance, can be implemented as a inductive power pick-up such as including an inductive coil and other appropriate circuitry that can receive, filter and couple power (e.g., via mutual inductance) from a corresponding power transmitter that may be placed adjacent or in contact with the power receiver. The power receiver 150 and the battery charging system 148 can be implemented as an integrated system to facilitate charging the battery 140. Additionally, the control system 102 can control the battery charging system 148 in response to the feedback 144. For example, the control system 102 can provide corresponding control signals 151 to the battery charging system 148 through a corresponding interface 152. Additionally, the current and/or voltage associated with the charging of the battery (or other parameters associated with operation of the charging system) can be monitored by the control system 102 via one or more corresponding analog inputs 154 that is provided to the ADC 146. The control system 102 can control the battery charging process in response to the voltage and/or current characteristics associated with the charging process, as detected via the input 154.

Figure 4:
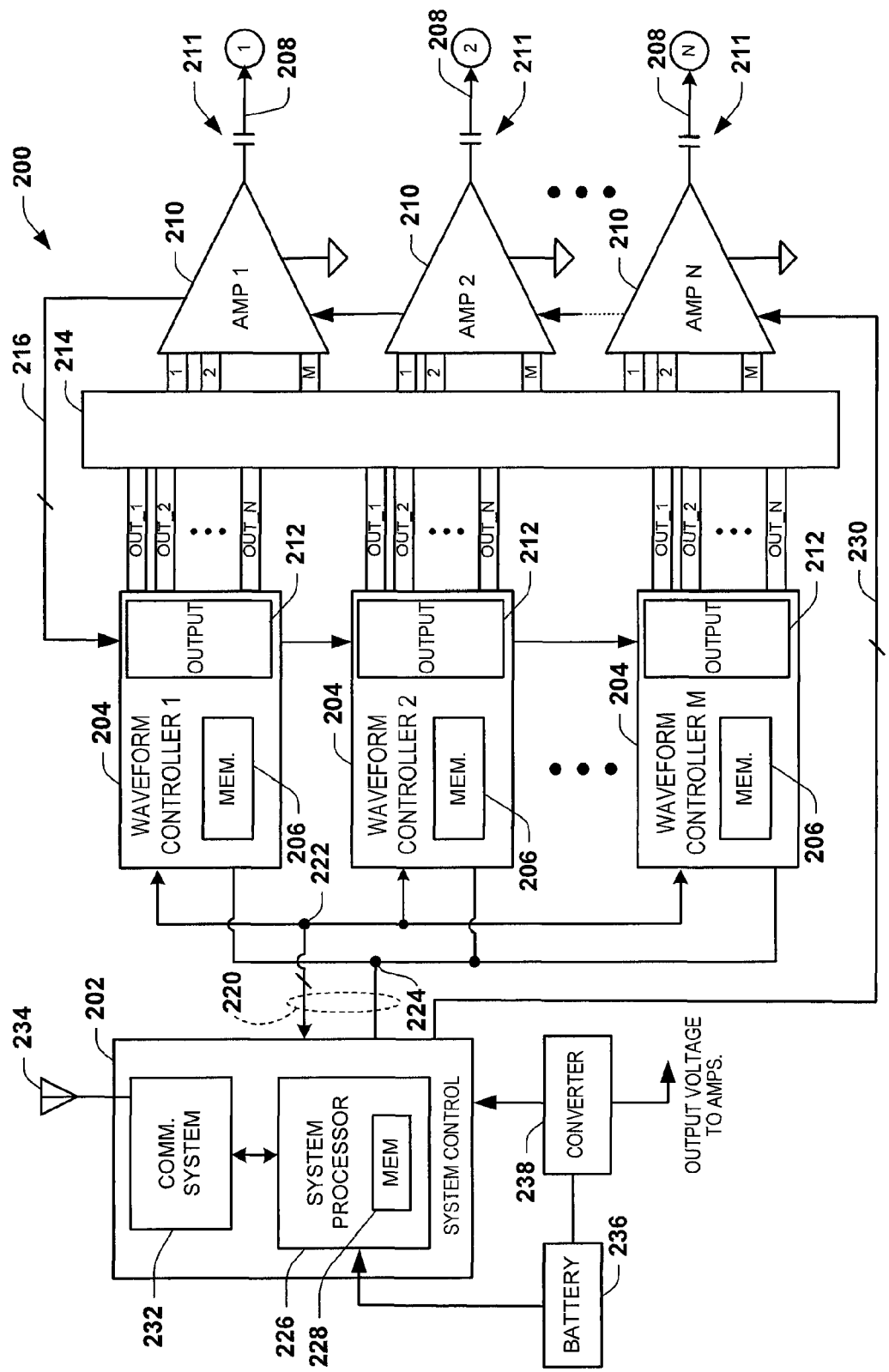
FIG. 4 depicts a block diagram of another embodiment of an implantable pulse generator system that can be implemented according to an aspect of the present invention.

FIG. 4 depicts another example of an IPG system 200 according to an embodiment of the present invention. The IPG system 200 includes a system control block 202. The system control 202 is programmed and/or configured to control basic operation of the system 200. The basic operation can include power management, communication and output controls. The system control 202 can also program one or more waveform controllers 204. As described herein, each of the waveform controllers 204 include memory 206 that can store waveform data representing one or more waveforms.

In the example of FIG. 4, there are M waveform controllers 204 (indicated at WAVEFORM CONTROLLER 1 through WAVEFORM CONTROLLER M), where M is a positive integer. Each waveform controller 204 is programmed to retrieve one or more waveform from its respective memory 206 for playback over one or more output channels 208. For example, there are N output channels, where N is a positive integer where $N \geq 1$. As one example, N=M; although, N may not be equal to M (e.g., N>M or N<M).

An amplifier 210 can be connected to drive each of the respective output channels 208. FIG. 4 depicts a separate amplifier 210, indicated at AMP 1, AMP 2 through AMP N, for driving each of the respective N output channels 208. Additionally, each amplifier 210 can be connected to a respective output channel through a DC blocking capacitor 211 to reduce inter-channel interference. By way of example, each of the amplifiers 210 can drive its associated output channel 208 based on a set of one or more waveform signals provided by one or more of the waveform controllers 204.

Each waveform controller 204 can include an output system 212 that controls to which of the N output channels 208 each respective waveform controller 204 provides its output waveform signal. The output system 212 thus selectively distributes output waveform signals to one or more output channels, such as based on a selection signal (not shown). For instance, each output system 212 can be electrically connected with an input of each of the N amplifiers 210 through a connection matrix 214. The connection matrix 214 may include a set of connections (e.g., electrically conductive wires or traces) that directly connect each of the M waveform controllers 204 and each of the N amplifiers. Alternatively, the connection matrix 212 can provide for a selected subset of connections from the waveform controllers to the amplifiers 210. Each amplifier 210 may include the same or a different number of inputs.

In some cases, a given amplifier 210 may receive an input waveform from only a single waveform controller 204. However, the design of FIG. 4 affords flexibility in which the given amplifier 210 can receive output waveforms from more than one waveform controller 204. For example, the system control 202 can provide instructions to each of the waveform controllers 204 to control to which set of one or more amplifier 210 the waveform controller provides its output waveform. Additionally, the system control 202 can program which respective waveform (either a single wave or train of multiple waveforms) are to be provided by each of the waveform controllers 204 to the respective amplifiers.

To support multiple input waveforms, the amplifiers 210 can include an input stage (e.g., summing circuitry—not shown) that aggregates the input waveforms received via the connection matrix 214. Each of the amplifiers 210 thus can overlay multiple waveforms received from the waveform controllers 204 to form a composite waveform that is, in turn, amplified and provided to the corresponding output channel 208.

The amplifiers 210 can also provide feedback, indicated schematically at 216, to the waveform controllers 204. For example, the feedback 216 can provide an indication of impedance for the respective output channels 208. The waveform controllers 204 can employ the impedance to ascertain whether the system 200 is operating within expected operating parameters (e.g., for placement of an electrode or for implementing safety features), such as described herein. The waveform controllers 204 can implement appropriate action based on the feedback received, including adjusting an output waveform or even terminating an output waveform from being provided to one or more of the amplifiers 210. The waveform controllers 204 can also provide information to the system control 202 based on the feedback 216.

As another example, the feedback 216 can provide an indication of charge associated with the electrode(s) being driven by a given amplifier 210. The waveform controller 204 can be programmed to compute charge density based on input parameters and known electrical characteristics of the electrode devices connected to the respective output channels 208. If the charge density exceeds a predetermined threshold, the waveform controller 204 can deactivate the output channel. It is to be appreciated that such computations can alternatively be performed by the system control 202 (e.g., depending on the processing ability afforded the waveform controllers).

Still another example might be to perform charge balancing in the operation of the amplifiers 210 based on feedback 216 received from the respective output channels 208. The monitoring of the charge at a given channel 208, for instance, can help ensure that no net DC voltage appears in any of the channels 208. The DC voltage for a given channel 208 can be mitigated, at least in part, by employing the DC blocking capacitors 211.

Those skilled in the art will understand and appreciate various types of amplifiers 210 that can be utilized to amplify the input waveforms (from the waveform controllers 204) for driving the output channels 208. The type of amplifier will typically be selected to provide for low power consumption since the IPG 200 is intended to be implanted in a subject. As one example, the amplifiers 210 can be implemented as class G amplifiers, which by adjusting the power supply voltage (or voltage rails) during operation, reduced power consumption can be achieved relative to other amplifier types. As another example, the amplifiers 210 can be implemented as class H amplifiers, which operate similar to class G amplifiers as well as modulate the output based on the input signal. Other types of amplifiers can also be utilized, such as amplifiers designed to amplify audio signals and also operate with low power consumption (e.g., class D or switching power amplifier).

As mentioned above, the system control system 202 can communicate with the waveform controllers 204, such as over a data bus 220. The bus 220 can be bi-directional to allow communication of information between the system control 202 and one or more of the waveform controllers 204. As one example, the bus 220 can be implemented as a serial peripheral interface (SPI) bus that communicates SPI data 222, such as including a clock signal, a "data in" signal, and a "data out" signal. The bus 220 can also include a "chip select" signal 224 to enable communication of the SPI data (data and clock signals) between the system control 202 and a selected one of the waveform controllers 204. Those skilled in the art will appreciate that system 200 may also implement other bus topologies, such as $I^2C$ bus, system management bus (SM-Bus), as well as other known or yet to be developed bus structures (e.g., including other serial and parallel bus structures).

As described herein, the system control 202 can employ the bus 220 to program each of the waveform controllers 204 as well as to receive information from the waveform controllers. According to one aspect, the system control 202 can program some or all of the waveform controllers 204 by storing one or more waveforms in the memory 206 for subsequent play back. The system control 202 can also program the waveform controller 204 to control which of the stored waveforms are to be played back during operation. The system control 202 can also program operation of the output system 212 of each of the waveform controllers 204 to control to which amplifier 210 the analog output waveforms are to be provided.

As another example, the system control 202 can program the waveform controllers 204 to adjust or scale parameters of the waveform(s) that are being played back. For example, the parameters can include amplitude, pulse width, and pulse duration. The system control 202 can also program the waveform controllers 204 to control the number of pulse trains of the one or more stored waveforms that are supplied as the corresponding analog output waveform. As described herein, the waveforms that are stored in the memory 206 of the respective waveform controllers 204 can be pre-recorded waveforms (recorded from an animal or from a waveform generator) or the waveforms can be synthesized waveforms that are provided to the system 200 as they are generated remotely.

The waveform controllers 204 can also provide information to the system control 202 via the bus 220. The waveform controllers 204 can provide information to the system control 202 in response to an interrogation command from the system control or automatically in response to detecting one or more predetermined conditions. For example, one or more of the waveform controllers 204 can provide impedance information to the system control based on the feedback 216 received from one or more amplifiers (e.g., raw feedback data and/or preprocessed information indicating detected impedance is outside of expected operating parameters). Other diagnostic information associated with operation of the waveform controllers 204 or as may be sensed by one or more sensors (not shown) can also be sent from the waveform controllers to the system control 202. This information may be stored in the memory 228 and acted on by one or more processes running in the system control 202. Alternatively, some or all such information can be sent to a remote station (e.g., an external programmer) via a communication system 232.

The system control 202 includes a system processor 226 and associated memory 228. For example, the system processor 226 can be implemented as a microcontroller unit that includes the memory 228. Alternatively or additionally, the memory 228 can be implemented separately from they system processor 226.

The memory 228 can include instructions and data to control the overall operation of the system 200. For instance, the memory 228 can store instructions and information to enable communication with the waveform controllers 204 over the bus 220. The memory 228 can also store instructions that define which of the amplifiers 210 are to be activated as well instructions that define operating parameters of the respective amplifiers (collectively referred to as "amplifier control instructions"). The system control 202 thus can employ the amplifier control instructions to provide corresponding control signals, indicated at 230, to control each of the amplifiers 210. The control signals 230, for example, can activate a given amplifier 210 as well as place a deactivated amplifier into a sleep mode (e.g., for power conservation). The control signals 230 can also adjust one or more amplifier operating parameters, such as to adjust amplifier gain or to adjust voltage rails for a respective amplifier. The memory 228 can also store scheduling information can identify which waveform or combination of waveforms are to be played back by each of the waveform controllers 204 as well as parameters of the respective waveforms that are to be played back.

The memory 228 can also store waveform data representing the waveforms that are being programmed into the waveform controllers. The waveforms can be stored in the memory 228 temporarily (e.g., during programming) or copies of all waveforms can be stored in the memory until erased or overwritten. The copies of waveforms stored in the memory 228 can provide a set of stored waveforms (internal to the IPG) that can be employed for programming the waveform controllers 204. For example, if adjustments need to be made to one or more waveforms (e.g., during operation), the adjustments may be made by the system control 202 selecting one or more alternative waveforms from the memory 228 and programming corresponding waveform controllers 204. Adjustments can also be implemented by appropriate scaling of waveform parameters. Alternatively, the one or more alternative waveforms can be provided from a remote external programmer, such as described herein.

The communication system 232 is coupled with an antenna 234 for communicating information wirelessly relative to the IPG. As mentioned herein, the information can include program instructions effective to control operation of the IPG system 200, including the system control 202, the waveform controllers 204 and the amplifiers 210. The system control 202 can receive such program instructions and store them in the memory 228, some of which can be transferred to program respective waveform controllers 204 via the bus 220.

The communication system 232 can be implemented as including a receiver and a transmitter (a transceiver) that provide for bi-directional communication of information relative to the IPG 200. A remote station thus can communicate with the IPG by employing a predetermined wireless protocol. The communication system 232 can implement any one of a plurality of known wireless communication protocols, such as Bluetooth, Digital Enhanced Cordless Telecommunications (DECT), OBject Exchange (OBEX) communication protocol, as well as other known and yet to be developed protocols.

The communication system 232 can also employ security features to inhibit unintentional or unauthorized access to the IPG 200. The security features can be part of the communication protocol being implemented by the communication system 232 or the features can be specific to the IPG system 200. For the example of implementing Bluetooth wireless communications, the communication system 232 can implement the SAFER+ algorithm for authentication and key generation. Alternatively, the use of a predefined key or ID associated with the IPG 200 may be required as part of data transmission to identify a communication as being an authorized communication.

The IPG 200 also includes a battery 236 that stores energy for providing power to the IPG. The battery 236 can include one or more cells configured to store a charge for providing corresponding DC voltage. The battery 236 can be replaceable and/or rechargeable depending on the expected duration that the IPG 200 will be implanted in a patient. The battery 236 can be directly coupled to the system control 202 and provide an output voltage to a power converter 238. The power converter 238 can provide a suitable regulated output voltage to the system control 202 and to the amplifiers 210 and the waveform controllers 204. The particular voltage provided by the converter 238 can vary based on the operating requirements of the circuitry implemented in the IPG system 200. Additionally, the amplifiers (e.g., if implemented as class G or H amplifier) 210 can implement load tracking functions, such as to adjust voltage rails as a function of the load requirements of the analog output waveforms being provided to the output channels 208.

Figure 4A:
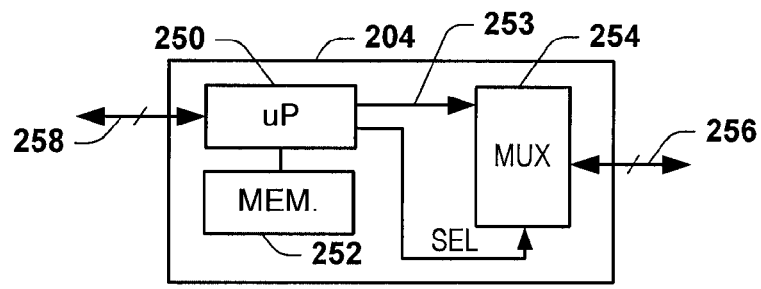
FIG. 4A depicts a block diagram of one type of waveform controller that can be employed in the system of FIG. 4.
Figure 4B:
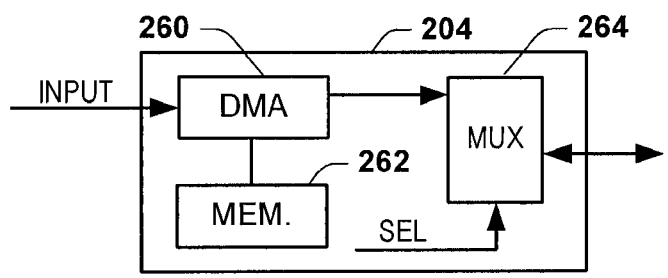
FIG. 4B depicts a block diagram of another type of waveform controller that can be employed in the system of FIG. 4.

FIGS. 4A and 4B depict examples of different basic configurations that can be utilized to implement the waveform controllers 204 of FIG. 4. In FIG. 4A, the waveform controller includes a processor 250 and associated memory 252. The memory 252 can be internal to the processor 250, external to the processor as shown, or a portion of the memory can be internal and another part can be external relative to the processor. The processor 250 is also coupled to supply an output waveform signal 253 to a multiplexer 254. The processor 250 supplies the output waveform signal 253 based on one or more waveforms retrieved from the memory 252. The multiplexer 254 distributes the output waveform signal to one or more selected outputs 256 for play back over a selected set of one or more output channels. For instance, the processor 250 can provide a selection signal (SEL) to the multiplexer 254 to control which channel amplifiers receive the output waveform via the outputs 256. It will be appreciated that that the waveform controller also includes digital-to-analog converter (not shown) to convert the stored digital waveform data into a corresponding analog output waveform that is provided to the selected outputs 256.

The waveforms can be stored in the memory 252 in response to waveform data provided to the waveform controller, such as from the system control 202 (FIG. 4). Control instructions can also be stored in the memory 252 to provide for other closed loop control of the waveform controller and the amplifiers being driven with the analog output waveforms. For instance, the processor 250 can also receive one or more signals, indicated at 258, from the amplifiers 210 or from sensors (not shown). The processor 250 can utilize the one or more signals 258 to adjust one or more parameters of the output waveform, to select one or more alternative waveforms, or to adjust operation of the amplifiers 210. By employing the processor 250 and memory 252 in the waveform controller, those skilled in the art will understand and appreciate various types of intelligent control that can be implemented at the waveform controller (e.g., including real time and/or periodic adjustments).

FIG. 4B depicts an example of another waveform controller 204 that includes a direct memory access (DMA) controller 260 that is connected with associated memory 262. The DMA controller 260 is programmed and/or configured to transfer one or more predetermined blocks of data from the memory 262 to an output multiplexer 264. As described herein, the blocks of data correspond to one or more waveforms that are stored in the memory 262. The system control 202 (FIG. 4), for example, can provide an INPUT signal to cause the DMA controller 260 to write the waveform data to the memory 262 (e.g., during a programming mode). The system control 202 can also program the DMA controller 260 to retrieve and transfer the stored waveform data to the multiplexer 264 (e.g., during normal operation). The system control 202 can also program the multiplexer 264 to distribute the corresponding analog output waveform to one or more amplifiers 210. For example, a corresponding selection signal (SEL) can be provided to configure the multiplexer 264 to distribute the output waveform to a selected set of one or more amplifiers 210. The SEL signal can be stored in the waveform controller, such as based on instructions from the system control 202 (FIG. 4).

It will be appreciated that variations of the basic approaches of FIGS. 4A and 4B may also be implemented. For instance, a processor and a DMA controller may be implemented in the waveform controller 204 so that play back of stored waveform(s) can be implemented by the DMA controller and other intelligent controls are executed by the processor. This combined approach can help reduce the processing requirements of the processor, although generally at the expense of additional circuitry to implement the DMA controller. The cooperation of the processor and the DMA controller may also be balanced according to the power requirements of the IPG 200. Additionally, those skilled in the art will appreciate other aspects and features that may be implemented in the waveform controllers of FIGS. 4A and 4B (e.g., including buses, connections and power inputs and filters).

Figure 5:
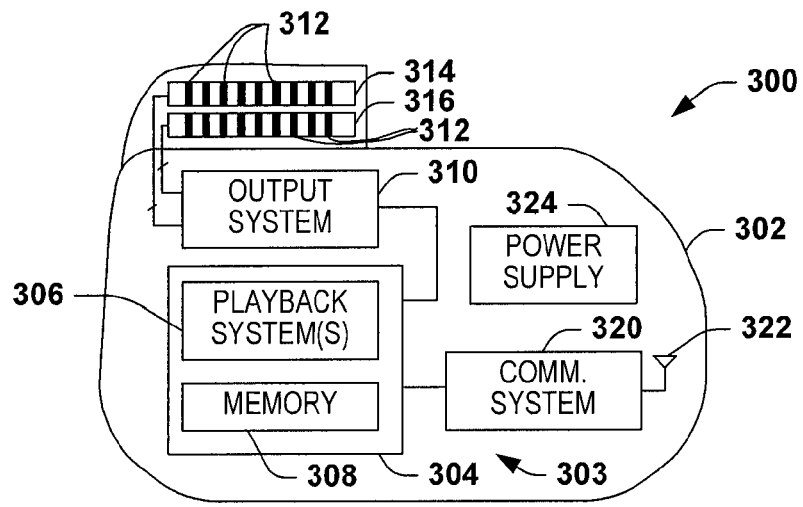
FIG. 5 depicts an example of an implantable pulse generator device that can be implemented according to an aspect of the present invention.

FIG. 5 depicts an example of an IPG 300 that may be implemented according to an aspect of the present invention. The IPG 300 includes a substantially biocompatible housing 302 that encapsulates IPG circuitry 303 that is programmed (or programmable) and configured to implement the functions described herein. The IPG circuitry 303 can correspond to any of the types of systems shown and described herein (e.g., FIGS. 1-4) as well as combinations thereof consistent with the teachings contained in this document. The housing 302 can be hermetically sealed. The circuitry 303 can include a control system 304 that can include a play back system 306 and memory 308, such as described herein. The control system 304 can provide one or more analog output waveforms (from the memory) to an associated output system 310. The output system 310 distributes one or more output waveforms to channels 312 associated with each of a plurality of respective output ports. As described herein, the waveforms provided to each channel 312 can be the same or different.

In the example of FIG. 5, a pair of output receptacles 314 and 316 each provides electrical access to the plurality of output channels 312. For instance, each channel can include an electrical contact that can be electrically connected to a corresponding mating part of a lead system (not shown). One type of lead system includes male connector parts that are dimensioned and configured for mating insertion into and within corresponding female receptacles 314 and 316 (e.g., the leads are plugged into the receptacles). The playback system 306 thus can deliver a corresponding amplified electrical stimulus to one or more electrodes (through the lead system) according to the output waveform delivered to each of the respective output channels 312. The number of leads and number channels for each receptacle can vary according to patient and pathology requirements.

The IPG 300 also includes a communication system 320 that is configured to enable communication with an external programmer (see, e.g., FIG. 2). For instance, the communication system 320 can employ wireless communication according to a predetermined communication mode via one or more antenna 322. The control system 304 can communicate with the external programmer via the control system. The communication may be bi-directional. For example, the control system 304 can receive program instructions and waveform data that can be stored in the memory, such as described herein. Additionally, the control system 302 can send diagnostic information and report on operating parameters of the IPG system 300 and of lead system that may coupled to the IPG system, such as described herein.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the spirit and scope of the appended claims.

What is claimed is:

1. A method for neuromodulation to treat a movement disorder, comprising:
   recording an input waveform from a first site in the nervous system in a source subject while the source subject is performing a task, wherein the first site is selected from the group consisting of: motor cortex, premotor cortex, thalamus, red nucleus, olivary nucleus, and dentate nucleus; and
   applying an output waveform to a second site in the nervous system in a target subject suffering from the movement disorder while the target subject is performing the same task, wherein the second site is selected from the group consisting of: motor cortex, premotor cortex, thalamus, red nucleus, olivary nucleus, and dentate nucleus;
   wherein the output waveform is identical to the input waveform or derived from the input waveform.

2. The method of claim 1, wherein the source subject and target subject are different subjects.

3. The method of claim 2, wherein the source subject is a non-human primate.

4. The method of claim 2, wherein the second site in the nervous system anatomically corresponds to a structure that is neurologically distal to the first site in the nervous system.

5. The method of claim 1, wherein the source subject and target subject are the same subject.

6. The method of claim 5, wherein the second site is the corresponding anatomic structure that is contralateral to the first site.

7. The method of claim 6, wherein the first site is healthy or at least partially functioning, and wherein the second site is diseased.

8. The method of claim 5, wherein the second brain site is neurologically distal from the first brain site.

9. The method of claim 1, further comprising positioning an electrode at the second site, and applying the output waveform through the electrode.

10. The method of claim 1, further comprising modifying the input waveform to generate the output waveform.

11. The method of claim 1, further comprising sensing a body activity.

12. The method of claim 11, further comprising, in response to the body activity sensed, modifying the output waveform.

13. The method of claim 12, wherein the body activity being sensed is limb motion.

14. The method of claim 1, wherein the task is a forelimb or hindlimb motor task.

15. The method of claim 1, further comprising: combining a plurality of different input waveforms to form a composite output waveform.

16. A method for neuromodulation to treat a movement disorder, comprising:

recording an input waveform from a first site in the nervous system in a source subject, wherein the first site is selected from the group consisting of: motor cortex, premotor cortex, thalamus, red nucleus, olivary nucleus, and dentate nucleus; and applying an output waveform to a second site in the nervous system in a target subject suffering from the movement disorder, wherein the second site is selected from the group consisting of: motor cortex, premotor cortex, thalamus, red nucleus, olivary nucleus, and dentate nucleus;

wherein the output waveform is identical to the input waveform or derived from the input waveform wherein the second site in the nervous system anatomically corresponds to the first site in the nervous system.

* * * * *